US010271882B2

(12) United States Patent
Biedermann et al.

(10) Patent No.: US 10,271,882 B2
(45) Date of Patent: Apr. 30, 2019

(54) BONE SCREW

(75) Inventors: Lutz Biedermann, VS-Villingen (DE);
Wilfried Matthis, Weisweil (DE);
Jürgen Harms, Karlsruhe (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 12/958,914

(22) Filed: Dec. 2, 2010

(65) Prior Publication Data
US 2011/0137352 A1 Jun. 9, 2011

Related U.S. Application Data

(60) Provisional application No. 61/266,382, filed on Dec. 3, 2009.

(30) Foreign Application Priority Data

Dec. 3, 2009 (EP) .................................. 09 177 909

(51) Int. Cl.
*A61B 17/86* (2006.01)
*A61B 17/88* (2006.01)

(52) U.S. Cl.
CPC ........ *A61B 17/8635* (2013.01); *A61B 17/864* (2013.01); *A61B 17/8685* (2013.01);
(Continued)

(58) Field of Classification Search
CPC ... A61B 17/86; A61B 17/8605; A61B 17/861; A61B 17/8615; A61B 17/8625; A61B 17/863; A61B 17/8635; A61B 17/864; A61B 17/8665; A61B 17/8685; A61B 2017/8655; F16B 25/00; F16B 25/0005; F16B 25/0036; F16B 25/0042; F16B 25/0057; F16B 25/0063; F16B 25/0084; F16B 25/0094; F16B 25/103;
(Continued)

(56) References Cited

U.S. PATENT DOCUMENTS 3,115,804 A * 12/1963 Johnson ........................ 411/338
3,411,396 A 11/1968 Herpich
(Continued)

FOREIGN PATENT DOCUMENTS

JP 05-060119 A 3/1993
JP 09149906 A 6/1997
(Continued)

OTHER PUBLICATIONS

Servip, AT—Search dated Dec. 11, 2009, 6 sheets.
(Continued)

*Primary Examiner* — Kevin T Truong
*Assistant Examiner* — Tracy Kamikawa
(74) *Attorney, Agent, or Firm* — Lewis Roca Rothgerber Christie LLP

(57) ABSTRACT

A bone screw includes a tubular body including a wall having a bone thread in at least a portion of an outer portion of the wall, an open first end and a second end. A plurality of cutting teeth is provided at the open first end, and a head is provided at the second end. An insert in the tubular body is configured to guide a wire therethrough.

28 Claims, 5 Drawing Sheets

(52) U.S. Cl.
CPC ....... *A61B 17/8605* (2013.01); *A61B 17/8615* (2013.01); *A61B 17/8625* (2013.01); *A61B 17/8897* (2013.01)

(58) Field of Classification Search
CPC ............. Y10T 407/19; Y10T 407/1952; Y10T 407/1962; Y10T 407/1964
USPC ........... 606/300–331; 30/113.1, 355; 407/30; 411/31, 387.1–387.8, 386, 395, 396
See application file for complete search history.

(56) References Cited

U.S. PATENT DOCUMENTS

| | | | | |
|---|---|---|---|---|
| 3,467,209 | A | * | 9/1969 | Chromy ........................ 175/395 |
| 4,013,071 | A | * | 3/1977 | Rosenberg ......... A61B 17/8685 411/397 |
| 4,484,570 | A | | 11/1984 | Sutter et al. |
| 4,537,185 | A | | 8/1985 | Stednitz |
| 5,584,629 | A | | 12/1996 | Bailey et al. |
| 5,827,285 | A | | 10/1998 | Bramlet |
| 5,964,767 | A | * | 10/1999 | Tapia et al. .................... 606/323 |
| 6,030,162 | A | | 2/2000 | Huebner |
| 6,077,267 | A | | 6/2000 | Huene |
| 6,079,923 | A | | 6/2000 | Ross et al. |
| 6,120,511 | A | * | 9/2000 | Chan ............................... 606/96 |
| 6,283,973 | B1 | | 9/2001 | Hubbard et al. |
| 6,508,818 | B2 | * | 1/2003 | Steiner et al. .................. 606/71 |
| 6,517,542 | B1 | | 2/2003 | Papay et al. |
| 6,517,543 | B1 | * | 2/2003 | Berrevoets ............. A61B 17/68 411/324 |
| 6,565,572 | B2 | * | 5/2003 | Chappius ....................... 600/300 |
| 6,743,233 | B1 | * | 6/2004 | Baldwin ............ A61B 17/0401 606/232 |
| 6,755,835 | B2 | | 6/2004 | Schultheiss et al. |
| 7,172,595 | B1 | * | 2/2007 | Goble ................. A61B 17/1714 606/86 A |
| 7,188,554 | B2 | | 3/2007 | Baynham |
| 7,261,716 | B2 | | 8/2007 | Strobel et al. |
| 9,198,702 | B2 | | 12/2015 | Biedermann et al. |
| 9,770,277 | B2 | | 9/2017 | Biedermann et al. |
| 9,827,028 | B2 | | 11/2017 | Biedermann et al. |
| 2001/0007072 | A1 | * | 7/2001 | Steiner et al. ................... 606/57 |
| 2004/0006345 | A1 | | 1/2004 | Vlahos et al. |
| 2004/0015172 | A1 | * | 1/2004 | Biedermann et al. .......... 606/73 |
| 2004/0068261 | A1 | * | 4/2004 | Fourcault et al. .............. 606/67 |
| 2004/0122431 | A1 | | 6/2004 | Biedermann et al. |
| 2004/0147929 | A1 | | 7/2004 | Biedermann et al. |
| 2004/0225292 | A1 | | 11/2004 | Sasso et al. |
| 2005/0055026 | A1 | * | 3/2005 | Biedermann ...... A61B 17/1659 606/278 |
| 2005/0101961 | A1 | | 5/2005 | Huener et al. |
| 2005/0107791 | A1 | | 5/2005 | Manderson |
| 2006/0247642 | A1 | | 11/2006 | Stone et al. |
| 2007/0025827 | A1 | * | 2/2007 | Pryor ......................... 411/387.1 |
| 2007/0162028 | A1 | * | 7/2007 | Jackson ............. A61B 17/8635 606/86 A |
| 2007/0233102 | A1 | | 10/2007 | Metzinger |
| 2008/0004627 | A1 | * | 1/2008 | Dalton ............................ 606/73 |
| 2008/0039846 | A1 | * | 2/2008 | Lee et al. ........................ 606/63 |
| 2008/0132959 | A1 | | 6/2008 | Mikkonen et al. |
| 2008/0154314 | A1 | | 6/2008 | McDevitt |
| 2008/0161864 | A1 | | 7/2008 | Beck et al. |
| 2009/0018590 | A1 | * | 1/2009 | Dorawa et al. ................ 606/301 |
| 2009/0210016 | A1 | | 8/2009 | Champagne |
| 2009/0248089 | A1 | * | 10/2009 | Jacofsky et al. .............. 606/311 |
| 2009/0270929 | A1 | * | 10/2009 | Suddaby ............ A61B 17/1637 606/324 |
| 2009/0281580 | A1 | * | 11/2009 | Emannuel .......... A61B 17/8625 606/304 |
| 2009/0318981 | A1 | | 12/2009 | Kang |
| 2011/0060373 | A1 | | 3/2011 | Russell et al. |
| 2011/0137354 | A1 | | 6/2011 | Biedermann et al. |

FOREIGN PATENT DOCUMENTS

| | | |
|---|---|---|
| JP | 10-211213 | 8/1998 |
| JP | 2004-512895 A | 4/2004 |
| JP | 2007-275573 A | 10/2007 |
| WO | WO 01/26568 A1 | 4/2001 |
| WO | WO 02/38054 A2 | 5/2002 |
| WO | WO 02/067759 A2 | 9/2002 |
| WO | WO 2004/069031 A2 | 8/2004 |

OTHER PUBLICATIONS

Extended European Search Report of Application No. EP 09 17 7909, dated Jan. 28, 2010, 6 sheets.
Office action for U.S. Appl. No. 12/958,898, dated Apr. 25, 2013 (13 pages).
Final Office action for U.S. Appl. No. 12/958,898, dated Feb. 25, 2014 (18 pages).
Office action for U.S. Appl. No. 12/958,898, dated Dec. 26, 2014 (22 pages).
Final Office action for U.S. Appl. No. 12/958,898, dated Sep. 8, 2015 (17 pages).
Office action for U.S. Appl. No. 12/958,898, dated Sep. 22, 2016 (33 pages).
Office action for U.S. Appl. No. 13/034,574, dated Jan. 30, 2013 (14 pages).
Office action for U.S. Appl. No. 13/034,574, dated Nov. 6, 2013 (12 pages).
Final Office action for U.S. Appl. No. 13/034,574, dated Aug. 25, 2014 (16 pages).
Office action for U.S. Appl. No. 13/034,574, dated Dec. 29, 2014 (7 pages).
Office action for U.S. Appl. No. 14/952,418, dated Apr. 14, 2016 (14 pages).
Office action for U.S. Appl. No. 12/985,183, dated Oct. 24, 2012 (9 pages).
Final Office action for U.S. Appl. No. 12/985,183, dated Apr. 12, 2013 (10 pages).
Office action for U.S. Appl. No. 12/985,183, dated Jun. 5, 2014 (12 pages).
Final Office action for U.S. Appl. No. 12/985,183, dated Dec. 22, 2014 (14 pages).
Office action for U.S. Appl. No. 12/985,183, dated Sep. 18, 2015 (14 pages).
Final Office action for U.S. Appl. No. 12/985,183, dated Mar. 17, 2016 (17 pages).
Office action for U.S. Appl. No. 12/985,183, dated Oct. 19, 2016 (9 pages).
Final Office action for U.S. Appl. No. 12/985,183, dated Mar. 13, 2017 (8 pages).

* cited by examiner

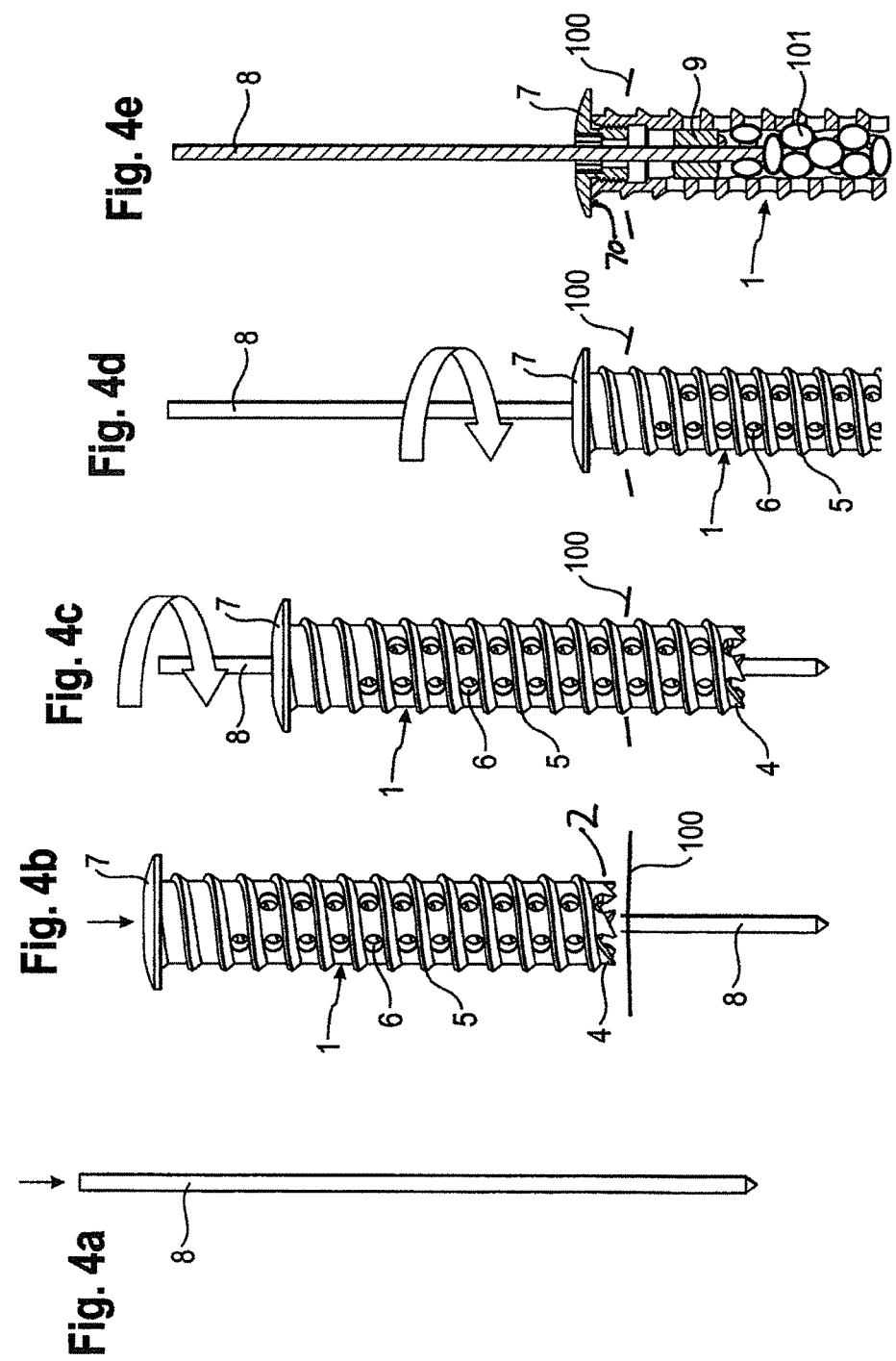

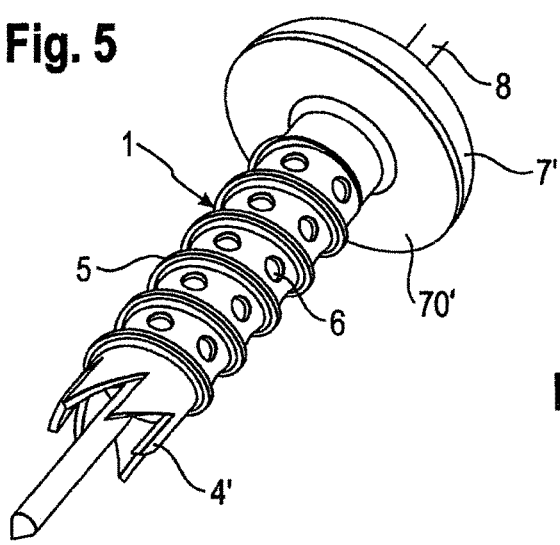
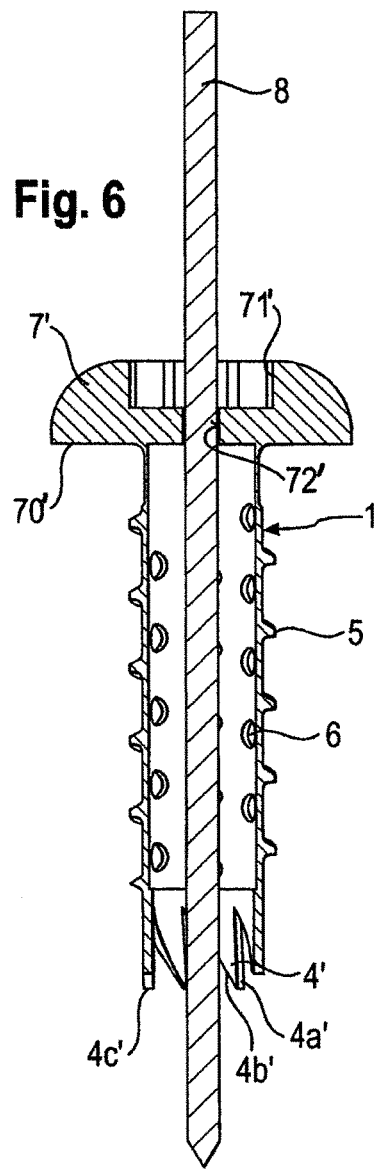
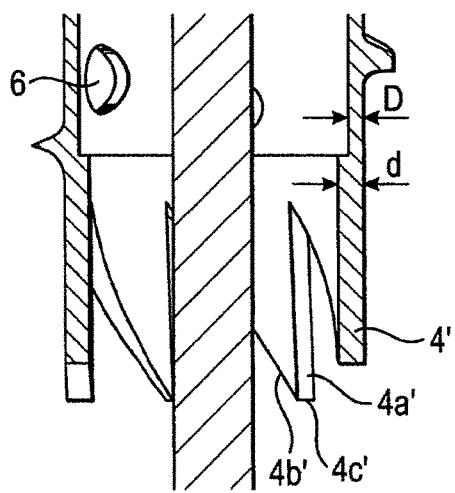

Fig. 12
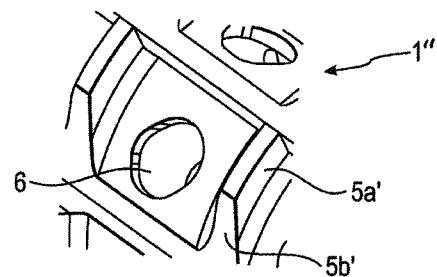
Fig. 13a      Fig. 13b
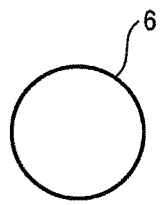    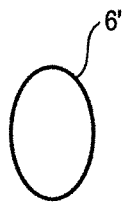
Fig. 13c      Fig. 13d
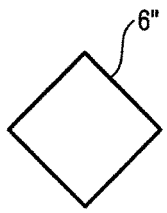    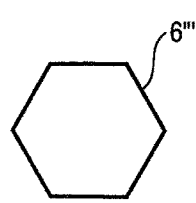

BONE SCREW

CROSS-REFERENCE TO RELATED APPLICATIONS

This Application claims priority to and the benefit of U.S. Provisional Application No. 61/266,382, filed Dec. 3, 2009, the entire contents of which are incorporated herein by reference. This Application also claims priority to and the benefit of EP 09 177 909.0, filed in the European Patent Office on Dec. 3, 2009, the entire contents of which are incorporated herein by reference.

BACKGROUND

The invention relates to a bone screw. In particular, the invention relates to a bone screw that can be used as a fusion screw. This screw promotes fusion in the surrounding bone.

A bone screw of this kind is known from US 2004/0015172 A1. This bone screw has a tubular thread section with a bone thread and with a plurality of recesses in its wall. A head and a tip can be connected to the tubular thread section. In use, the tubular portion can be filled with bone material or other growth-promoting material and then the tip and/or the head are connected to the tubular portion. First, a core hole is prepared, then the screw is inserted into the core hole and screwed into the bone. After a certain period, fusion between the screw and the bone takes place. The screw can act as a traction element to connect shattered or split off parts of bones together by means of the screw. To avoid the preparation of a core hole, the tip can be self-cutting.

Similar bone screws are known for example from US 2004/0122431 and US 2004/0147929 A1.

Further, so-called injection screws, for example such as described in WO 01/26568 A1 are known, which are used to inject bone cement or other liquid or pasty material into the bone. This kind of screw has a relatively thin cannula extending within a bone screw. The cannula is not suitable for being filled with bone chips or bone graft.

SUMMARY

It is the object of the invention to provide a bone screw that can be quickly screwed into the bone without using a prepared core hole.

The bone screw according to the invention is self-filling. When it is screwed into the bone the cutting teeth engage the bone and create a hole. The bone material from the location at which the screw is inserted fills the cavity of the tubular body. Hence, the preparation of a core hole is not necessary. It is not necessary to pre-fill the tubular body with bone material. Therefore, the procedure of implanting the bone screw is less time consuming than in a case where the bone screw has to be pre-filled and inserted into a core hole prepared in advance. Furthermore, the bone material has a more intact structure compared to pre-filled bone material, which could enhance the healing process.

The bone screw is particularly suitable for strong healthy bones and for weak osteoporotic bones, since the structural damage that occurs when screwing-in the bone screw can be kept to a minimum.

By using a guide wire procedure for insertion, the bone screw can be used in minimally invasive surgery.

Further features and advantages of the invention will become apparent from the description of various embodiments of the invention by means of the accompanying drawings.

BRIEF DESCRIPTION OF THE DRAWINGS

FIG. 1 shows an exploded perspective view of a first embodiment of the bone screw.

FIG. 2 shows the bone screw of FIG. 1 in an assembled state.

FIG. 3a shows the tubular body that is part of the bone screw of FIGS. 1 and 2 in a sectional view with an insert for the guide wire being in a first location.

FIG. 3b shows the tubular body that is part of the bone screw of FIGS. 1 and 2 in a sectional view with the insert being in a second location.

FIG. 4a) to 4d) show steps of inserting the bone screw according to the first embodiment in the bone.

FIG. 4e shows a cross-sectional view of the bone screw according to the first embodiment in the bone.

FIG. 5 shows a perspective view of a second embodiment of the bone screw.

FIG. 6 shows a sectional view of the bone screw of FIG. 5.

FIG. 7 shows an enlarged portion in a sectional view of the bone screw according to FIGS. 5 and 6 in the region of the cutting teeth.

FIG. 12 shows an enlarged perspective view of a detail of the wall portion of the bone screw according to FIGS. 8 to 11.

FIG. 13a) to 13d) show variations of the shape of the openings provided in the wall of the bone screw according to the previous embodiments.

DETAILED DESCRIPTION

Figures 1, 2, 3A, 3B:
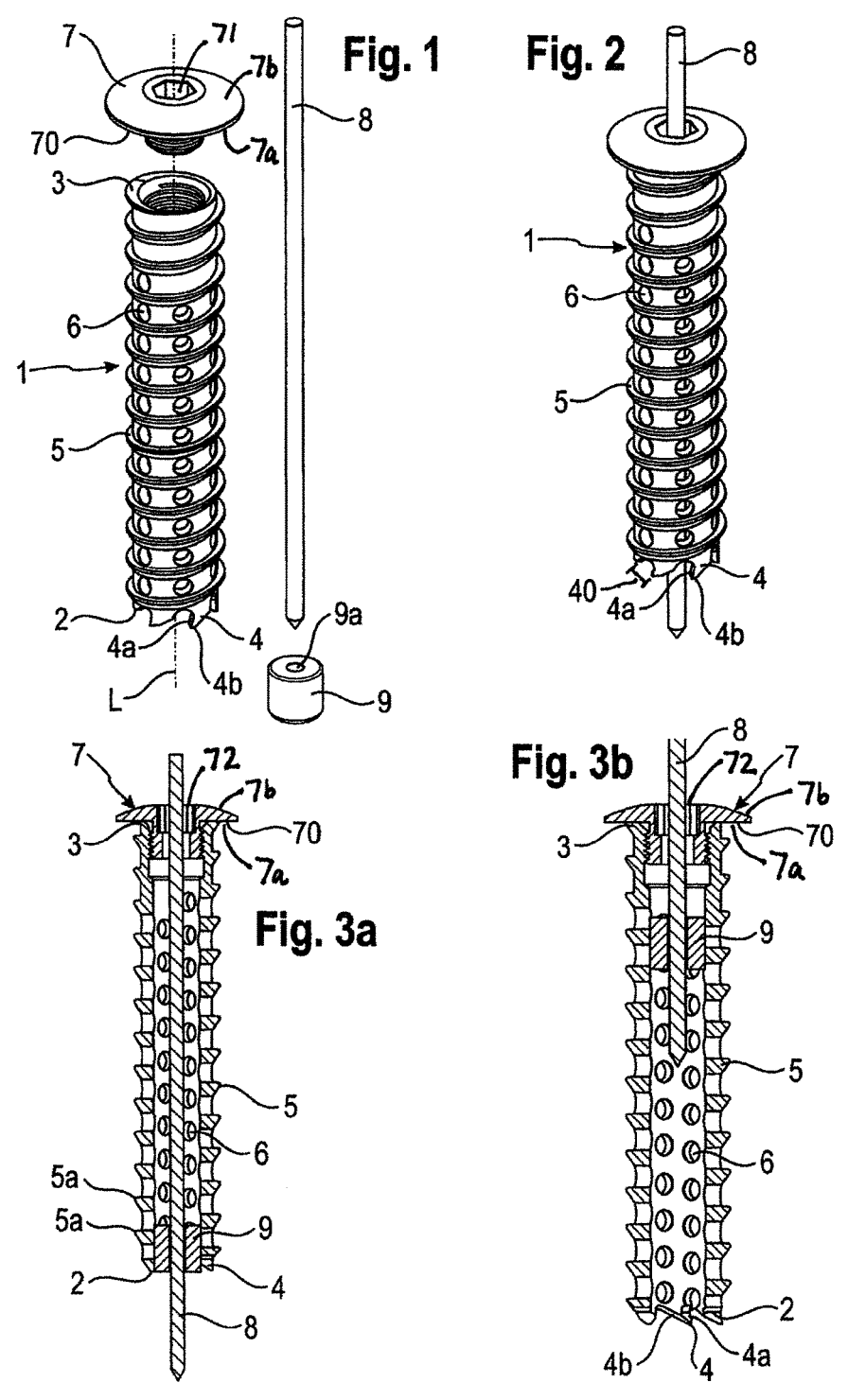
Figure 8:
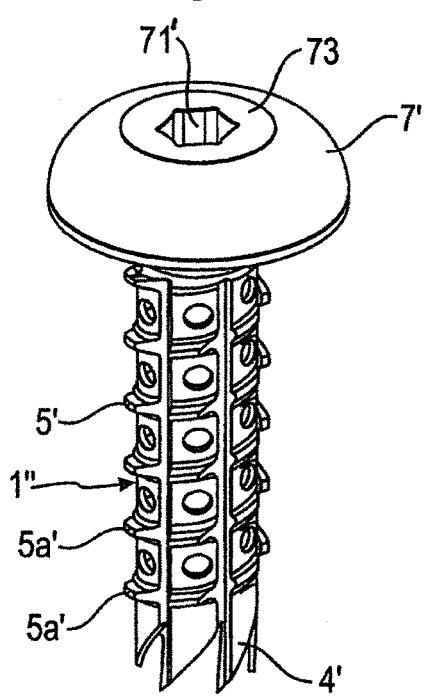
FIG. 8 shows a perspective side view of a modification of the second embodiment of the bone screw.

A bone screw according to a first embodiment as shown in FIGS. 1 to 4 comprises a tubular body 1 with an open first end 2 and a second end 3 and a central longitudinal axis L. At the first end 2, the free edge of the tubular body comprises a plurality of cutting teeth 4 that are configured to cut a hole into the bone. In a portion of its outer wall, the tubular body 1 comprises a so-called bone thread 5. This portion is adjacent to the first end 2, as shown in the embodiment. The bone thread 5 is configured to cut into the bone when the bone screw is screwed-in into the bone. Although, the figures show a bone thread with a substantially saw-tooth shape, all kinds of known bone threads can be used. The cutting teeth 4 extend from the edge of the first end 2 coaxially to the longitudinal axis L. In the embodiment shown, they are substantially saw tooth-shaped. This shape includes a steep flank 4a that extends in an angle of larger than 45° with respect to a circumferential line along the free edge and a shallow flank 4b that extends under an angle of between 0° and 45° with respect to the circumferential line along the free edge. In order to ease the insertion of the screw, the steep flanks are oriented all in the same circumferential direction. Between each of the cutting teeth 4 there is a distance 40 in the circumferential direction to facilitate the cutting. The cutting teeth are configured to cut a ring-shaped hole into the bone. Within the hole, bone material remains. The bone material that remains in between the cutting teeth is accommodated in the tubular body. It can consist either of chips or it can be a plug-like coherent mass or both.

The height of the cutting teeth is in the embodiment shown smaller than the width of the root between two crests 5a of adjacent turns of the bone thread 5.

The thickness of the cutting teeth in a radial direction can be larger than a thickness of the wall of the tubular body, as shown in FIG. 7. This results in providing an enlarged space within the tubular body to accommodate the bone material.

The shape and the number of the cutting teeth can vary. All kinds of cutting teeth are suitable that are configured to cut the bone such that bone material remains inside the tubular body.

As shown in the Figures, in the wall of the tubular body, a plurality of openings 6 are provided to allow in-growth of bone material and vessels from the surrounding of the bone screw. The openings 6 are shown as circular holes and extend completely through the wall of the tubular body 1. They are located between the crests of the bone thread 5. However, any other variations of the shapes and locations of the openings 6 are conceivable. In the embodiment shown, the cutting teeth 4 are located at the free edge 2 between two openings 6, which further enhances their cutting ability.

At the second end 3 a separate head 7 is connectable to the tubular body 1. The connection can be a threaded connection as shown, a press-fit connection or any other connection. The head 7 has a first side 7a facing the tubular body 1 and a second side 7b opposite to the tubular body. The first side 7a may include a flat portion 70 that can serve as an abutment for the bone surface when the bone screw is screwed-in. On its upper side 7b opposite to the tubular body the head 7 has an engagement structure 71 for engagement with a screw driver. Furthermore, the head 7 has a central hole 72 that is coaxial with the longitudinal axis L of the tubular body for guiding a guide wire 8 therethrough. Further, a cylindrical insert 9 with a hole 9a for guiding the guide wire 8 therethrough can be accommodated in the tubular body 1. The insert 9 is designed to be movable within the tubular body between a position near the first end 2, shown in FIG. 3a, to a position near the second end 3, shown in FIG. 3b. The guide wire 8 has a length that is greater than the length of the bone screw so that in minimally invasive surgery ("MIS"), the bone screw can be guided along the guide wire 8 to the implantation site and maintain the proper orientation.

Although the tubular body 1 is shown to be cylindrically-shaped, other shapes are conceivable. For example, the tubular body 1 may have close to the first end 2 a reverse tapered section tapering away from the first end 2. The cavity provided by the tubular body 1 has a volume that is suitable for accommodating bone material. The wall thickness of the tubular body is preferably smaller than about 15% of the screw core diameter.

All parts of the bone screw are made of a body compatible material such as a body compatible metal, for example stainless steel or titanium; a body compatible metal alloy, for example Nitinol; or a body compatible plastic material, for example PEEK.

In addition, the tubular body or the other parts of the bone screw can be coated with an in-growth promoting material or can be roughened to enhance in-growth of bone or vessels.

FIGS. 4a) to 4d) show the use of the bone screw according to the first embodiment in minimally invasive surgery ("MIS"). First, as shown in FIG. 4a), the guide wire 8 is introduced through the skin of the patient and advanced through the tissue until it reaches the position where the bone screw is to be placed. Then, the guide wire is inserted into the bone to the appropriate direction and depth. As shown in FIG. 4b), the bone screw with assembled tubular body 1 and head 7 is guided along the guide wire 8 extending therethrough until it reaches the surface 100 of the bone. At first, the insert 9 is located near the first end 2 of the tubular body. Next, as shown in FIGS. 4c) and d) the bone screw is screwed into the bone guided by the guide wire. The cutting teeth 4 generate the hole for the screw, and the bone thread 5 facilitates further advancement of the bone screw into the hole.

As shown in FIG. 4e), bone material 101 that is scraped off by the cutting teeth 4 fills the interior of the tubular body 1. During the insertion of the bone screw into the bone, the insert 9 is shifted into the direction towards the second end 3 of the tubular body. The bone screw may be advanced until the flat portion 70 of the head 7 abuts against the bone surface 100.

Finally, the guide wire 8 is retracted.

After some time has passed, the bone material in the tubular body fuses with bone material surrounding the bone screw so that the bone screw is rigidly connected to the bone. By means of this, particularly broken bone parts or instable bones can be firmly connected or weak osteoporotic bone can be stabilized.

In a further modification, the tubular body has a non threaded section preferably adjacent to the second end 3. In such a case the bone screw can be used, for example, as a tension screw that holds together broken bone parts or instable bones by tension.

FIGS. 5 to 6 show a second embodiment of the bone screw. Portions that are the same as those of the first embodiment are indicated with the same reference numerals. The second embodiment differs from the first embodiment in the head 7' and in the shape of the cutting teeth 4'.

The cutting teeth 4' are longer than the cutting teeth 4 of the previous embodiment and have a sharper tip 4c' provided by the steep flank 4a' and the shallow flank 4b', the latter being steeper than in the first embodiment. Also, there is no distance or only a small distance between the cutting teeth 4' in a circumferential direction.

As can be seen in particular in FIG. 7, the thickness d in a radial direction of the cutting teeth 4' is larger than the thickness D of the wall of the tubular body. Therefore, when the bone screw is screwed into the bone, the bone material that results from the cutting process of the cutting teeth 4' can fill a space in the tubular body 1 that is larger in the radial direction than the space between the cutting teeth. This facilitates advancement of the bone screw into the bone.

Different from the first embodiment, the head 7' is made in one piece with the tubular body 1. This facilitates handling of the whole bone screw, since the step of connecting the head with the tubular body is not necessary.

As in the first embodiment the head 7' has an engagement portion 71' for engagement with the screw driver and a flat portion 70' that can provide an abutment to the bone. Further, a hole 72' for guiding the guide wire 8 therethrough is provided.

The use of the bone screw according to the second embodiment is similar to that of the first embodiment and is therefore, not repeated.

FIGS. 8 to 12 show a bone screw according to a modification of the second embodiment. All parts that are identical to the second embodiment as shown in FIGS. 5 to 6 are referenced with the same reference numerals and the description is not repeated. In the modified embodiment, the crests of the bone thread 5' on the outer wall of the tubular body 1" are interrupted at regular distances, i.e. crest portions 5a' are arranged on a helical line around the outer wall of the tubular body 1". The crest portions 5a' are shown in an enlarged view in FIG. 12. They may have inclined surfaces 5b' extending in the direction of the helix and in a reverse direction. The length of the crest portions 5a' in the direction of the helix can vary.

Figure 9:
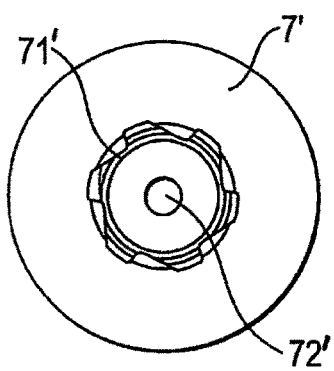
FIG. 9 shows a top view of the bone screw according to FIG. 8.
Figure 10:
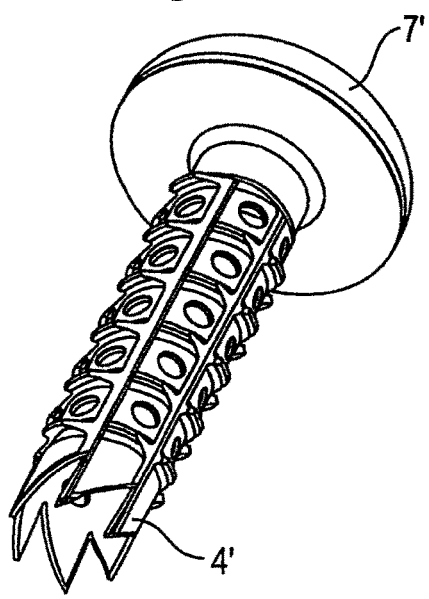
FIG. 10 shows another perspective view of the bone screw of FIG. 8.
Figure 11:
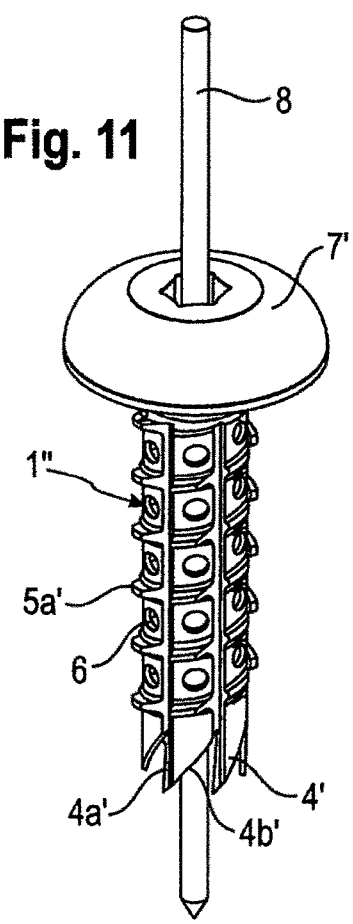
FIG. 11 shows a perspective side view of a further modification of the bone screw of FIG. 8.

In addition, the head 7' may have an insert portion 73 having the engagement portion 71' and the guiding hole 72' as shown in FIGS. 8 and 9.

As shown in FIGS. 13a) to 13d) the openings 6, 6', 6", 6'" can have various shapes such as circular as shown in FIG. 13a), oval as shown in FIG. 13b), diamond shaped as shown in FIG. 13c), hexagon shaped as shown in FIG. 13d), or otherwise shaped.

The embodiments do not limit the invention. Various heads can be provided according to the specific needs. It is also conceivable that the head is a head portion of a monoaxial or polyaxial bone screw that is configured to include a rod that connects several bone screws. The diameter and length of the tubular body and the number and shape of the cutting teeth can vary according to the actual clinical requirements. Moreover, with any of the aforementioned embodiments, the wall in the vicinity of the plurality of cutting teeth is thicker in a radial direction than the wall adjacent the plurality of cutting teeth.

The invention claimed is:

1. A bone screw comprising:
   a tubular body having a longitudinal axis, the tubular body comprising a wall comprising a plurality of openings through said wall, said wall having a first end and a second end, and defining a bore having an open first end opposite a second end, a bone thread on at least a portion of an outer surface of the wall, and a plurality of cutting teeth at the open first end; and
   a monolithic head comprising a shaft that is configured to be inserted into the bore at the second end of the wall and configured to be connected to the second end of the wall inside the bore, the head having a surface defining a hole through the head, wherein the surface is exposed to the bore and the hole is in communication with the bore when the entire bone screw is implanted into a body, said hole having a first diameter;
   the monolithic head configured to abut a bone in the body when the entire bone screw is implanted into the body;
   wherein a region of the wall at the plurality of cutting teeth is thicker in a radial direction than a region of the wall adjacent to the plurality of cutting teeth;
   wherein the bore at the plurality of cutting teeth has an inner second diameter greater than the first diameter when the bore is entirely open therethrough, wherein said hole is aligned with the bore;
   wherein the plurality of cutting teeth form an edge of the open first end and are configured to drill a hole when the tubular body is screwed into the bone; and
   wherein at least a portion of the bone thread is on part of the outer surface of the wall adjacent to the plurality of cutting teeth.

2. The bone screw according to claim 1, wherein the plurality of cutting teeth extend coaxially to the longitudinal axis of the tubular body.

3. The bone screw according to claim 1, wherein each of the plurality of cutting teeth has a shape resembling a tooth of a saw.

4. The bone screw according to claim 1, wherein the tubular body comprises a non-threaded section.

5. The bone screw according to claim 1, wherein the head comprises a structure for engagement with a screw driver.

6. The bone screw according to claim 1, wherein the head is a separate part that can be connected to the tubular body.

7. The bone screw according to claim 1, wherein the head has a first end facing the tubular body and a second end opposite to the tubular body and wherein the first end of the head provides the abutment to the bone in the body.

8. The bone screw according to claim 1, wherein the hole in the head is configured to guide a wire therethrough.

9. The bone screw according to claim 1, further comprising an insert, wherein the wall comprises a length as measured longitudinally from the first end of the wall to the second end of the wall, wherein the insert is configured to be provided in the wall of the tubular body and wherein the insert is configured to guide a wire therethrough, the insert being movable along the longitudinal axis of the wall of the tubular body and having an axial length that is shorter than the length of the wall of the tubular body.

10. The bone screw according to claim 1, wherein the bone thread is continuous.

11. The bone screw according to claim 1, wherein the bone thread is interrupted.

12. The bone screw according to claim 1, wherein the bone thread is interrupted at regular distances.

13. The bone screw according to claim 1, wherein the tubular body is cylindrical.

14. The bone screw according to claim 1, wherein an inner radius of the region of the wall at the plurality of cutting teeth is smaller than an inner radius of the region of the wall adjacent to the plurality of cutting teeth to form an enlarged space within the tubular body adjacent to the plurality of cutting teeth.

15. The bone screw according to claim 1, wherein the region of the wall at the plurality of cutting teeth defines said bore.

16. The bone screw according to claim 1, wherein the thread extends from adjacent the head to adjacent the plurality of cutting teeth.

17. The bone screw according to claim 1, wherein a radial thickness of the wall as measured at any location of the wall is less than 15% of an outer diameter of the wall.

18. The bone screw according to claim 1, wherein the head has a greater outer diameter than the tubular body.

19. The bone screw according to claim 1, wherein the connection is a threaded connection between the shaft and the wall.

20. A bone screw comprising:
   a tubular body having a longitudinal axis, the tubular body comprising a wall comprising a plurality of openings through said wall, said wall having a first end and a second end, and defining a bore having an open first end opposite a second end, a bone thread on at least a portion of an outer surface of the wall, and a plurality of cutting teeth at the open first end; and
   a monolithic head at the second end of the wall having a surface defining a hole through the head, wherein the surface is exposed to the bore and the hole is in communication with the bore when the entire bone screw is implanted into a body, said hole having a first diameter;
   the monolithic head configured to abut a bone in the body when the entire bone screw is implanted into the body;
   wherein a region of the wall at the plurality of cutting teeth is thicker in a radial direction than a region of the wall adjacent to the plurality of cutting teeth, and wherein a radial thickness of the wall as measured at any location of the wall is less than 15% of an outer diameter of the wall;

wherein the bore at the plurality of cutting teeth has an inner second diameter greater than the first diameter when the bore is entirely open therethrough, wherein said hole is aligned with the bore;

wherein the plurality of cutting teeth form an edge of the open first end and are configured to drill a hole when the tubular body is screwed into the bone; and wherein at least a portion of the bone thread is on part of the outer surface of the wall adjacent to the plurality of cutting teeth.

21. The bone screw according to claim 20, wherein the head and the tubular body are a monolithic piece.

22. A bone screw comprising:

a tubular body having a longitudinal axis, the tubular body comprising a monolithic wall having a bone thread on at least a portion of an outer surface of the wall, the wall having a first end and a second end and defining a bore having an open first end opposite a second end, the bone thread comprising a length as measured longitudinally from a first end of the bone thread to a second end of the bone thread, the wall further comprising a plurality of openings through said wall, and a plurality of cutting teeth at the open first end; and a head comprising a shaft that is configured to be inserted into the bore at the second end of the wall and configured to be connected to the second end of the wall inside the bore, the head having an opening therethrough in communication with the bore, said opening having a first diameter; and an insert having a hole configured to guide a guide wire therethrough and being completely insertable in the tubular body, the insert being movable within the tubular body between a position near the first end of the wall and a position near the second end of the wall, wherein said insert has an axial length that is shorter than the length of the bone thread;

wherein the bore at the plurality of cutting teeth has an inner second diameter greater than the first diameter, wherein said opening is aligned with the bore;

wherein the plurality of cutting teeth form an edge of the open first end and are configured to drill a hole when the tubular body is screwed into a bone;

wherein at least a portion of the bone thread is on part of the outer surface of the wall adjacent to the plurality of cutting teeth; and wherein the entire insert is movable into the bore without rotating the insert.

23. The bone screw according to claim 22, wherein the insert is configured to slide along an inner portion of the wall.

24. The bone screw according to claim 22, wherein the hole of the insert is a central borehole configured to allow the guide wire to pass through.

25. The bone screw according to claim 22, wherein the head comprises a structure for engagement with a screw driver, wherein the head has a first end facing the tubular body and a second end opposite to the tubular body and wherein the first end of the head provides an abutment to contact the bone in the body when the entire bone screw is implanted into the body.

26. The bone screw according to claim 22, wherein the opening of the head is configured to guide the guide wire therethrough.

27. The bone screw according to claim 22, wherein each of the plurality of cutting teeth comprises a leading flank, a trailing flank and a tip between the flanks when viewed in a radial direction and wherein the leading flank creates an angle with the trailing flank when viewed in the radial direction.

28. The bone screw according to claim 22, wherein the plurality of cutting teeth extend coaxially to the longitudinal axis of the tubular body, and wherein each of the plurality of cutting teeth has a shape resembling a tooth of a saw.

* * * * *